US008694085B2

(12) United States Patent
Reifman et al.

(10) Patent No.: US 8,694,085 B2
(45) Date of Patent: Apr. 8, 2014

(54) COLLECTION AND ANALYSIS OF VITAL SIGNS

(75) Inventors: Jaques Reifman, New Market, MD (US); Maxim Y. Khitrov, Rockville, MD (US); Andrew T. Reisner, Newtonville, MA (US); Liangyou Chen, Hanover Park, IL (US); Thomas McKenna, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/204,657

(22) Filed: Aug. 6, 2011

(65) Prior Publication Data

US 2012/0078128 A1  Mar. 29, 2012

Related U.S. Application Data

(60) Provisional application No. 61/401,179, filed on Aug. 6, 2010.

(51) Int. Cl.
*A61B 5/0432*  (2006.01)
(52) U.S. Cl.
USPC ........................................................ 600/523
(58) Field of Classification Search
USPC ............... 607/59, 30; 600/510, 513, 523–525
See application file for complete search history.

(56) References Cited

U.S. PATENT DOCUMENTS 5,683,432 A * 11/1997 Goedeke et al. ................ 607/32
6,182,245 B1    1/2001 Akin et al.
7,222,265 B1    5/2007 LeSuer et al.
7,899,687 B2    3/2011 Morris
2002/0058861 A1  5/2002 Drew
2006/0111933 A1  5/2006 Wheeler
2007/0094227 A1  4/2007 Randazzo et al.
2008/0133275 A1  6/2008 Haug et al.

FOREIGN PATENT DOCUMENTS

EP       1174816 A2     1/2002
WO    2010/035161 A1    4/2010

OTHER PUBLICATIONS

Chen, Liangyou, et al., "Algorithms to Qualify Respiratory Data Collected During the Transport of Trauma Patients," Physiological Measurement, 2006, pp. 797-816, vol. 27.
Chen, Liangyou, et al., "Automated Beat Onset an Peak Detection Algorithm for Field-Collected Photoplethysmograms," 31st Annual International Conference of the IEEE EMBS, Sep. 2-6, 2009, pp. 5689-5692.

(Continued)

*Primary Examiner* — George Evanisko
(74) *Attorney, Agent, or Firm* — Elizabeth Arwine; Cahn & Samuels, LLP (57) ABSTRACT

A system is disclosed having a storage, a communications module for interacting with a medical measurement device, an analysis controller, and a test module that allows for the testing and evaluating of decision-support algorithms. A method for testing decision-support algorithms is disclosed having the steps of receiving into storage of a ruggedized, compact computer at least one decision-support algorithm; detecting with a communications module the initiation of a vital-sign monitoring session; receiving and storing vital-sign information into storage by the communications module; pushing the stored vital-sign information by an analysis controller to a test module running the stored at least one decision-support algorithm; and providing at least one output from the decision-support algorithm to at least one of a database and a display.

14 Claims, 4 Drawing Sheets

(56) References Cited

OTHER PUBLICATIONS

Chen, Liangyou, et al., "Can We Improve the Clincial Utility of Respiratory Rate As a Monitored Vital Sign?", Shock, Jun. 2009, pp. 574-580, vol. 31, No. 6.

Chen, Liangyou, et al., "Decision Tool for the Early Diagnosis of Trauma Patient Hypovolemia," Journal of Biomedical Informatics, 2008, pp. 469-478, vol. 41.

Chen, Liangyou, et al, "Diagnosis of Hemorrhage in a Prehospital Trauma Population Using Linear and Nonlinear Multiparameter Analysis of Vital Signs," Proceedings of the 29th Annual International Conference of the IEEE EMBS, Aug. 23-26, 2007, pp. 3748-3751, IEEE.

Chen, Liangyou, et al., "Exploration of Prehospital Vital Sign Trends for the Prediction of Trauma Outcomes," Prehospital Emergency Care, Jul./Sep. 2009, pp. 286-294, vol. 13, No. 3.

Chen, Liangyou, et al., "Exploiting the Existence of Temporal Heart-Rate Patterns for the Detection of Trauma-Induced Hemorrhage," 29th IEEE EMBS Annual International Conference, Aug. 20-24, 2008, pp. 2865-2868.

Dietterich, Thomas G., "Ensemble Methods in Machine Learning," First International Workshop on Multiple Classifer Systems, Oregon State University, 2000, pp. 1-15, vol. 1857.

Drew, Guy A., et al., "An Advanced Time Synchronized Multimedia Multiplatform Biomedical Data Acquisition System," United States Army Institute of Surgical Research, 2002.

Edmonds, Zachary V., et al., "The Reliability of Vital Sign Measurements," Annals of Emergency Medicine, Mar. 2002, pp. 233-237, vol. 39, No. 3.

Feeley, Mike, "US Army Institute of Surgical Research Data Acquisition System for Hemorrhage Moves to Next Phase." U.S. Army Medical Research and Material Command, http://www.kmimediagroup.com/mmt-home/251-mmt-2010-volume-14-issue-4-june/3001-us-army-institute-of-surgical-research-data-acquisiti . . . , vol. 14, issue 4, Jun. 2001.

Fishcher, Sandra, et al., "Handheld Computing in Medicine," Journal of the American Medical Informatics Association, Mar./Apr. 2003, pp. 139-149, vol. 10, No. 2.

Grinstead, Brad, et al., "Biomedical Signal Acquisition Using Labview," Proceedings of the 11th IEEE Symposium on Computer-Based Medical Systems, 1998, pp. 157-161.

Garner, Dainel C., et al., "Noise in Medical Helicopters," JAMA, Jul. 24-31, 1991, pp. 515, vol. 266, No. 4.

Jung Insung, et al., "User Pattern Learning Algorithm Based MDSS (Medical Decision Support System) Framework under Ubiquitous," World Academy of Science, Engineering and Technology 36 2007, 2007, pp. 184-188.

Kittler, J., et al., "Sum Versus Vote Fusion in Multiple Classifier Systems," IEEE Transactions on Pattern Analysis and Machine Intelligence, Jan. 2003, pp. 110-115, vol. 25, No. 1.

Koenig, Steven C., et al., "Integrated Data Acquisition System for Medical Devices Testing and Physiology Research in Compliance with Good Laboratory Practices," Biomedical Instrumentation & Technology, May/Jun. 2004, pp. 2-13.

Kramer, George C., et al., "Closed-Loop Resuscitation of Hemorrhagic Shock," UTMB, Anesthesiology Resuscitation Research Laboratory, Final Report, Feb. 21, 2011.

Kuncheva, Ludmila I., "A Theoretical Study on Six Classifier Fusion Strategies," IEEE Transactions on Pattern Analysis and Machine Intelligence, Feb. 2002, pp. 281-286, vol. 24, No. 2.

Lovett, Paris B., et al., "The Vexatious Vital: Neither Clinical Measurements by Nurses Nor an Electronic Monitor Provides Accurate Measurements of Respiratory Rate in Triage," Annals of Emergency Medicine, Jan. 2005, pp. 68-76, vol. 45, No. 1.

Low, Ronald B., et al, "Accuracy of Blood Pressure Measurements Made Aboard Helicopters," Annals of Emergency Medicine, Jun. 1988, pp. 604-612, vol. 17, No. 6.

McKenna, Thomas M., et al., "The Physiology Analysis System: An Integrated Approach for Warehousing, Management and Analysis of Time-Series Physiology Data," Computer Methods and Programs in Biomedicine, Apr. 2007, pp. 62-72, vol. 86.

Musen, Mark A., et al., "Biomedical Infomatics: Computer Applications in Health Care and Biomedicine," 3rd Edition, 2006, pp. 698-736.

Norris, Patrick Roger, "Toward New Vital Signs: Tools and Methods for Physiologic Data Capture, Analysis, and Decision Support in Critical Care," Dissertation Submitted to the Faculty of the Graduate School of Vanderbilt University, May 2006.

Reifman, Jaques, et al., "Automated Decision-Support Technologies for Prehospital Care of Trauma Casualties," Nato Rto Human Factors & Medicine Panel Symposium, Use of Advanced Technologies and New Procedures in Medical Filed Operators, NATO OTAN, RTO-MP-HFM-182, Apr. 19-21, 2010, Essen, Germany.

Saleem, Mohammed, "Clincial Decision Support Systems," University of Connecticut, Computer Science and Engineering 300, May 5, 2008.

Tsien, Christien L., et al., "Poor Prognosis for Existing Monitors in the Intensive Care Unit," Critical Care Medicine, Apr. 1997, pp. 614-619, vol. 25, iss. 4.

Yu, Chenggang, et al., "A Method for Automatic Identification of Reliable Heart Rates Calculated form ECG and PPG Waveforms," Journal of the American Medical Informatics Association, May/Jun. 2006, pp. 309-320, vol. 13, No. 3.

National Instruments, "Options for Working with NI LabVIEW; The MathWorks, Inc. MATLAB Software; and M-File Scripts," NIWeek 2011, http://www.ni.com/analysis/matlab.htm.

Seeking Alpha, "Welch Allyn Adds Masimo Total Hemoglobin to Connex Vital Signs Monitors," Business Wire 2011, Jul. 14, 2011, http://www.seekingalhpa.com/news-article/1424024-welch-allyn-adds-masimo-total-hemoglobin-to-connex-vital-signs-monitor.

Drew, Guy A., et al., "Biomedical Patient Monitoring, Data Acquisition, and Playback with LabVIEW," Biomedical Test, Chap. 2, 2000, pp. 92-98.

Koenig, Steven C., et al., "Integrated Data Acquisition System for Medical Device Testing and Physiological Research in Compliance with Good Laboratory Practices," Biomedical Instrumentation & Technology, May/Jun. 2004, pp. 229-240, vol. 38.

Reisner, Andrew T., et al., "Automatically-Computed Prehospital Severity Scores are Equivalent to Scores Based on Medic Documentation," The Journal of Trauma Injury, Infection, and Critical Care, Oct. 2008, pp. 915-923, vol. 65, No. 4.

\* cited by examiner

COLLECTION AND ANALYSIS OF VITAL SIGNS

This application claims the benefit of U.S. provisional patent application No. 61/401,179 filed Aug. 6, 2010 and entitled "System for Real-Time Collection and Analysis of Vital Signs and Prediction of Clinical Outcomes," which is hereby incorporated by reference.

I. FIELD OF THE INVENTION

This invention relates to a system and method for developing, testing, and evaluating decision-support algorithms in a portable unit using stored data and/or real-life, real time data.

II. BACKGROUND OF THE INVENTION

Typically, decision-support algorithms are incorporated into vital-sign monitors and other medical recording systems. This results in the algorithms being proprietary to the manufacturer and not facilitating easy modification or refinement by end-users and/or testing of new decision-support algorithms by either the manufacturer or the end-users.

Most of the existing literature discusses research in the decision-support area that uses retrospective analysis of previously gathered data to test and refine decision-support systems located on workstations and/or servers.

III. SUMMARY OF THE INVENTION

The invention provides in at least one embodiment a system for receiving an output from an external source where the system includes: a storage; a communications module for receiving vital-sign data from an external source and storing the received data in said storage; an analysis controller in communication with said storage, said analysis controller monitors said storage; and a test module in communication with said analysis controller and said storage, said test module receives information from said storage through said analysis controller and stores any output in said storage, and said test module includes running means for running at least one algorithm loaded into said storage where said at least one algorithm processes at least a portion of the information provided by said analysis controller.

The invention provides in at least one embodiment a system for receiving vital-sign information from a vital-sign monitor, said system including: a storage having at least one database; a communications module for receiving vital-sign data from an external source and storing the received data in said database of said storage; an analysis controller in communication with said storage, said analysis controller monitors said storage; a test module in communication with said analysis controller and said storage, said test module receives information from said storage through said analysis controller, and said test module includes running means for running at least one algorithm loaded into said storage where said at least one algorithm processes at least a portion of the information provided by said analysis controller, said running means provides an output in substantially real time from receipt of vital-sign data by said communications module; a ruggedized, compact housing enclosing said storage, said communications module, said analysis controller, and said test module.

The invention provides in at least one embodiment a method for testing decision-support algorithms where the method includes: receiving into storage of a ruggedized, compact computer at least one decision-support algorithm; detecting with a communications module the initiation of a vital-sign monitoring session; receiving and storing vital-sign information into storage by the communications module; pushing the stored vital-sign information by an analysis controller to a test module running the stored at least one decision-support algorithm; and providing at least one output from the decision-support algorithm to at least one of a database and a display.

Given the following enabling description of the drawings, the invention should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements. The use of shading within the drawings is not intended as limiting the type of materials that may be used to manufacture the invention.

V. DETAILED DESCRIPTION OF THE DRAWINGS

FIGS. 1-4 illustrate different embodiments and aspects according to the invention.

In at least one embodiment, the system 100 is compact, which for this disclosure is defined as being easily moved and transported, for example, between a vehicle such as an ambulance or helicopter to a medical facility with the patient. Compact is further defined as smaller than a laptop and small relative to a vital-sign monitor 190 such as illustrated, for example, in FIG. 3. Compact is further defined by being of sufficiently small size to allow for use in the field away from established medical facilities.

In at least one embodiment, the system is ruggedized, which for this disclosure is defined as being able to substantially withstand vibration, shock, temperature, temperature shock, altitude, dropping, rain, dust, and humidity and remain substantially working and operational for its intended purpose.

In at least one embodiment, the system operates in real time, which for this disclosure is defined as storing and processing a continuous stream of vital-sign information (or data) as outputted by a vital-sign monitor where the processing includes any algorithm 1254 present in the test module 125 with substantially minimal lag time (e.g., allows for processing time by the algorithm(s) 1254).

Figure 1:
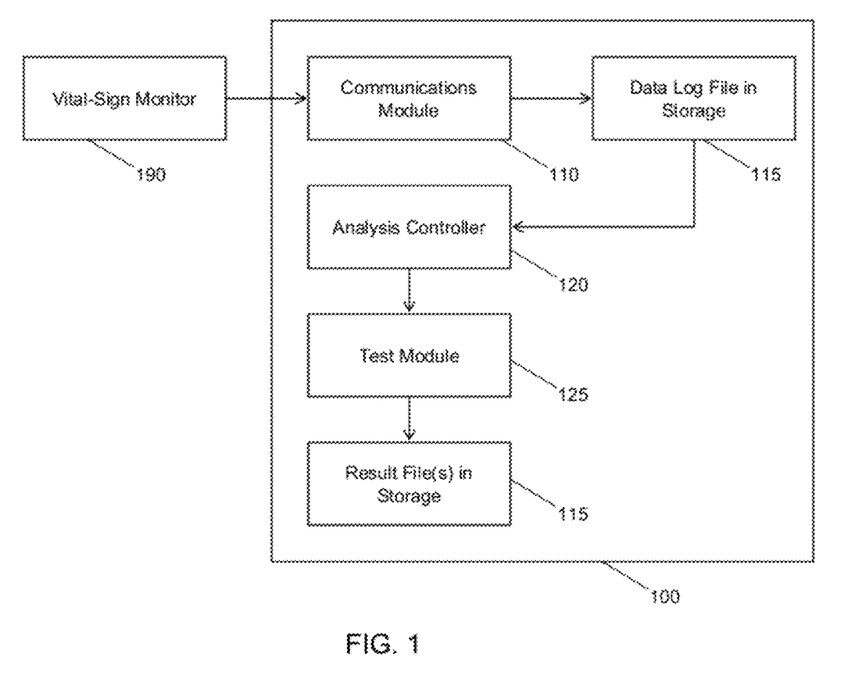
FIG. 1 illustrates a block diagram including a data flow according to an embodiment of the invention.

As illustrated in FIG. 1, the flow of data through at least one embodiment includes a system 100 having a communications module 110, a storage 115, an analysis controller 120, and a test module 125. The communications module 110 is in communication with the storage 115. The analysis controller 120 is in communication with the storage 115 and the test module 125, which in at least one embodiment is in communication with the storage 115. As used in this disclosure "in communication" includes physical and wireless connections that are indirect through one or more additional components (or over a network) or directly between the two components described as being in communication.

FIG. 1 also illustrates an example of how data will flow through at least one embodiment. The output of the vital-sign monitor (or other medical monitor or external source) 190 is received by the communications module 110 that stores the received data into storage (or memory) 115. In at least one embodiment, storage 115 includes a database for storing the received data. For the purposes of this disclosure, a database includes any type of list, data table, relational database, a text file, a comma delimited file, data log file, or a series of data files associated with one session. The analysis controller 120 monitors the storage 115 for the addition of new data that it will push to the test module 125. The test module 125 provides an environment in which a loaded algorithm(s) 1254 operates to produce a result based on at least a portion of the data pushed by the analysis controller 120. The produced result in at least one embodiment is provided to at least one of the storage 115 including, for example, the database used for the received data or a separate database; a display 130; or for transmission to an external device through, for example, a wired connection or an antenna 1054.

Figure 2:
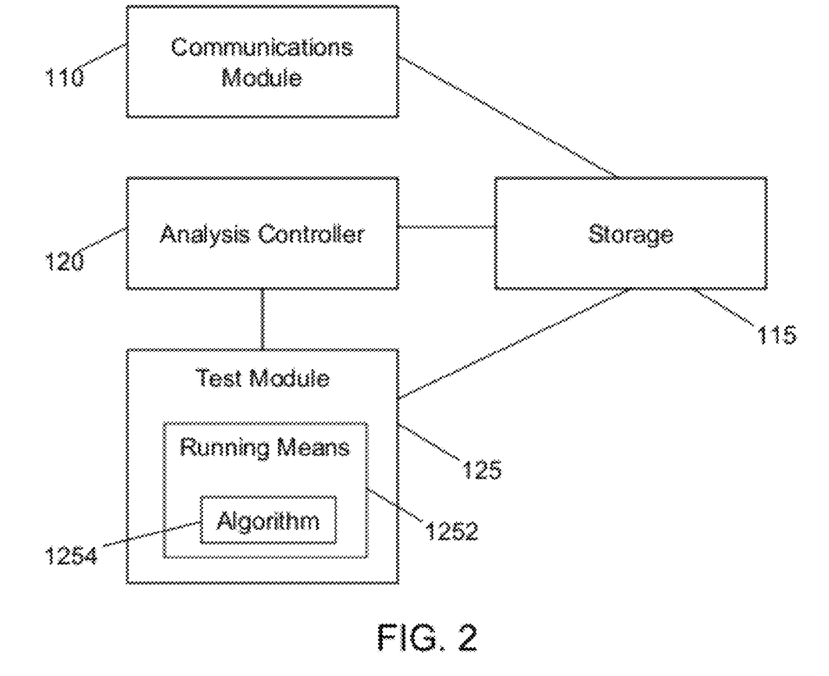
FIG. 2 illustrates a block diagram according to an embodiment of the invention.

FIG. 2 illustrates an embodiment similar to that of FIG. 1 without the flow of data being represented. FIG. 2 illustrates the system as including a communications module 110, a storage 115, an analysis controller 120, and test module 125.

The communications module 110 maintains the connection with the vital-sign monitor 190 and stores the received data (e.g., vital-sign information) into storage 115. The communications module 110 in at least one embodiment transmits a "keep-alive" (or similar) packet (or message) to the vital-sign monitor 190 to maintain the connection and avoid termination of the connection by the vital-sign monitor 190. The communications module 110 in at least one embodiment traps errors and recovers from communication errors using, for example, cyclic redundancy check to determine if corruption is present in the received packet of information. In addition in further embodiments, the communications module 110 uses a sequential packet number, which in at least one embodiment cycles through a set of numbers, present at the start of each packet to maintain the received packets in order prior to storage 115 of the received information, which is useful in a network environment with multiple paths between the vital-sign monitor and the communications module. For example, the Welch Allyn Propaq vital-sign monitors produce packets at different frequencies. Numerical data from the vital-sign monitor, such as heart rate, respiratory rate, blood oxygen saturation, and noninvasive systolic, diastolic, and mean blood pressures, are outputted at a frequency of 1 Hz (once per second). The electrocardiogram (ECG), photoplethysmogram (PPG), and impedance pneumogram (IP) are waveforms that are reported at 182 Hz, 91 Hz, and 23 Hz, respectively, and in at least one embodiment the packets are sent every 88 ms with each packet having 16, 8, and 2 data points, respectively. The communications module 110 stores these data packets as these packets are received and, if necessary, the communications module 110 arranges them in order prior to storing in the storage 115.

In at least one embodiment, the communications module 110 is in a standby state until it receives a numeric heart rate value greater than 10 beats per minute or between 10 and 350 beats per minute and ends a session when no such value is received for a 5-minute interval (although other time periods may be used), for example, any length of time in a range of 2 to 15 minutes (including the end points). The end of the session in at least one embodiment is based on a predetermined threshold of length of time (predetermined time threshold) of receipt values less than 10 beats per minute (predetermined vital-sign threshold). The requirement for a heart rate value indicative of life provides a reasonable basis to assume that the vital-sign monitor 190 is attached to a person. However, in alternative embodiments, another vital-sign such as $SpO_2$ is used to determine whether a patient is connected to the vital-sign monitor. In a further embodiment, a signal representing that a patient is connected or other status indication such as a "fault" state from ECG leads being cleared is provided by the vital-sign monitor 190 to the communications module 110 to indicate when a session has started and/or ended. The end condition reflects the case where the vital-sign monitor 190 is turned off or simply detached from the patient at the end of a medical session such as arrival at a medical facility. It is estimated that a one-hour session will require approximately 5 MB of disk space. In this embodiment, once the communications module 110 detects the start of a session, then it notifies and/or activates the analysis controller 120 and/or the test module 125 to start.

In a further embodiment, the communications module 110 timestamps the vital-sign information as part of the storing the information into storage 115. The timestamp allows for improved archival of the information and for review of the information outputted by the test module 125, which in at least one embodiment allows for further refinement of the algorithm(s) 1254 operating in the test module 125.

The storage 115 in at least one embodiment is computer storage 115 medium as defined later in this disclosure. An illustrative example of the storage 115 is a memory. Based on this disclosure, it should be appreciated that storage 115 also includes a plurality of discrete storages for the different data being stored in the system.

The analysis controller 120 monitors the physiological data logged into the storage 115 for the presence of new data in at least one embodiment. When new data are detected and/or a new session started, the analysis controller 120 pushes that data to the test module 125 by extracting the information from storage 115 and providing it in an appropriate syntax for use by the algorithm(s) 1254 operating in the test module 125.

In at least one embodiment, the analysis controller 120 converts the packet data into multiple constant-frequency row vectors. The vector in at least one embodiment has a length equal to the frequency multiplied by the time period (e.g., the example below has a vector length of 4). The analysis controller 120 aligns and/or shifts the data contained in the storage 115 to take into account any communication breaks and/or missing data. For example if the storage 115 contains the following data where Seq represents the packet number (or sequence):

Time=0, Seq=100, Data=[HR: 80, $SaO_2$: 98]
Time=1, Seq=101, Data=[HR: 82]
Time=3, Seq=103, Data=[HR: 81, $SaO_2$: 97]

The analysis controller 120 converts the information into two vectors (one for heart rate (HR) and one for oxygen saturation ($SaO_2$)):

HR=[80 82 NaN 81]
$SaO_2$=[98 NaN NaN 97]
where NaN (Not a Number) is representative of missing data, which in this example Sequence 101 was missing $SaO_2$ and Sequence 102 was missing in its entirety (or lost). The missing data was filled in with NaNs (although other fillers could be used to indicate the missing data) to preserve a frequency of 1 Hz for the data.

In an example where the sampling by the analysis controller 120 is to occur at 5 seconds, but the packet (Sequence 104) has not been stored in the storage 115. The analysis controller 120 in at least one embodiment includes a time threshold beyond which it will consider the packet to be lost.

In at least one embodiment, the analysis controller 120 pushes the data based on a predetermined sampling period to reduce the load on the test module 125 based on the algorithms being run in the test module 125. For example, in at least one embodiment, the analysis controller 120 retrieves the current data every 5 seconds although the algorithm(s) 1254 running in the test module 125 uses data at approximately 2 minute intervals. In at least one embodiment, the analysis controller 120 is implemented on a processor as a configurable shell.

The test module 125 hosts and runs at least one algorithm with examples of the algorithms including but not limited to the following functions: pattern recognition, generation of graphical displays, generation of text files, determination of data quality, prediction of patient outcome using for example artificial intelligence classifiers, analysis of time-series vital-sign data, etc. In at least one embodiment, the test module 125 includes running means 1252 for running the algorithm(s) 1254 such as a software environment running on a processor in which the code used to write the algorithm(s) is capable of functioning and interacting with the vital-sign information provided to it by the test module 125. The test module 125 retrieves at least one algorithm 1254 from storage 115 and runs it in response to data received from the analysis controller 120. In at least one embodiment, the analysis controller 120 and/or test module 125 restrict the frequency of data provided to the algorithm(s) 1254 to reflect the processing time required for the algorithm(s) 1254, which results in data being provided at predetermined time intervals with some data being ignored with the most recent values being used at the predetermined time intervals. By retrieving the algorithm(s) 1254 from storage 115, it allows for the algorithm(s) 1254 to be updated, modified, or changed by loading into the storage 115 the new/modified algorithm making it available for the next session.

The result produced by the algorithm(s) 1254 is provided by the test module 125 to at least one of the storage 115, the display 130, and an external device (not shown). In at least one embodiment, there are at least two algorithms running with the first algorithm reviewing the vital-sign information for quality control and providing a filtered output of the vital signs that pass quality control to the second or more algorithms running in the test module 125.

In at least one embodiment, the data placed into storage 115 is organized by session, which as used in this disclosure means a time period from when a patient is connected to a vital-sign monitor to the time that they are disconnected for a period longer than the predetermined time threshold discussed above from the vital-sign monitor.

The algorithms 1254 that are tested, evaluated and/or used in the above-described embodiments will need to use the data syntax used by the analysis controller 120. In at least one embodiment, the algorithm(s) 1254 will have as its respective input(s) at least a portion of the vital signs in a form that will be able to communicate with the analysis controller 120. In at least one embodiment, the test module 125 will discard vital signs not of interest to the algorithm(s) 1254; however, in other embodiments the test module 125 provides all vital signs received from the analysis controller 120 to the algorithm(s) 1254 with the algorithm(s) 1254 deciding what data it wants to use. In at least one embodiment, the test module 125 and the algorithm(s) 1254 are built using the same computer language or code such as MATLAB, C, or LabVIEW.

Figure 3:
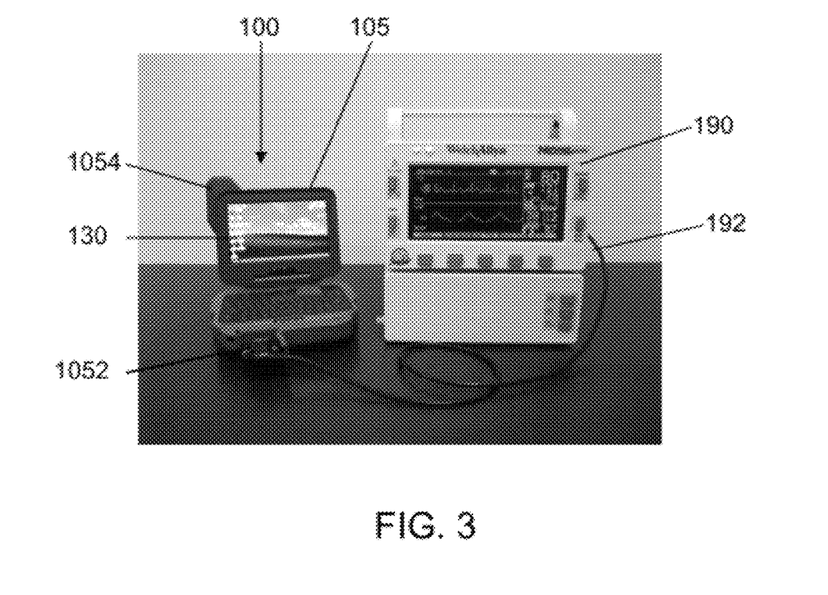
FIG. 3 illustrates an embodiment according to the invention.

FIG. 3 illustrates an example of an embodiment built according to the invention attached to a vital-sign monitor 190 such as the Propaq Encore sold by Welch Allyn although other vital-sign monitors could be used instead. There are a variety of ways for the system to communicate with a vital-sign monitor including but not limited to wireless or wired, such as a RS-232/USB cable adaptor or RS-232/serial cable adaptor 192. Based on this disclosure, it should be appreciated that there are a variety of additional ways that a vital-sign monitor 190 can be connected to the system besides the illustrated connector. FIG. 3 also illustrates an embodiment of the system including a display 130 and a housing 105 with a connector 1052. The illustrated system 100 was built with a test module 125 using MATLAB.

Figure 4:
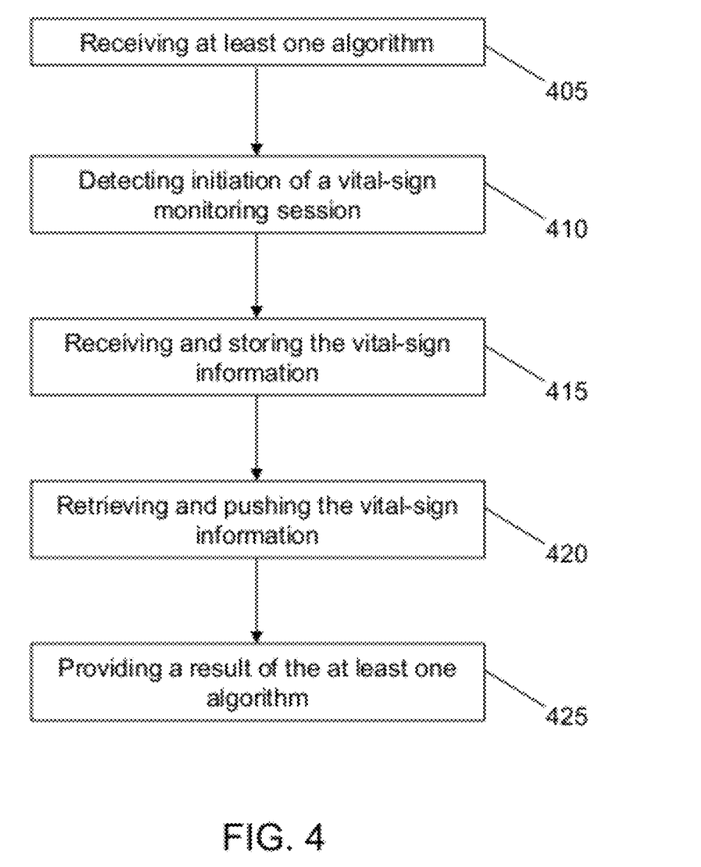
FIG. 4 illustrates a flowchart of a method embodiment according to the invention.

FIG. 4 illustrates a flowchart of a method embodiment according to the invention for using the system illustrated in FIG. 2. The illustrated method in at least one embodiment is for operation of a compact computer or a ruggedized, compact computer. In at least one embodiment prior to initiation of a session, the computer receives at least one algorithm into storage 115, 405. The algorithm(s) 1254 will be used by the test module 125 during a session. In at least one embodiment, the method includes detecting with the communications module 110 the initiation of a vital-sign monitoring session, 410. The communications module 110 receives and stores the vital-sign information into storage 115, 415. As discussed above in at least one embodiment, the analysis controller 120 retrieves the vital-sign information from storage 115 and pushes the vital-sign information to the test module 125 running the stored at least one decision-support algorithm 1254, 420. The test module 125 provides at least one output from the decision-support algorithm 1254 to at least one of a database 115 and a display 130, 425, or in an alternative embodiment to an external device by for example wireless transmission through an antenna 1054 of the output. In a further embodiment, the test module 125 outputs an audible alert when the algorithm(s) 1254 detects a critical condition or other predetermined situation. In a still further embodiment, the test module 125 retrieves the stored decision-support algorithm(s) 1254 from storage 115 after a session is initiated; or alternatively, the decision-support algorithm(s) 1254 is available in the test module 125 once received in storage 115.

In at least one embodiment, after multiple sessions are stored by the system, the stored data are transferred from the system for analysis and evaluation to determine whether the stored algorithm has functioned as intended and/or whether improvements should be made to the stored algorithm.

In at least one embodiment, the information captured by the system is stored or copied to a computer storage medium capable of removable form the system for transfer to the medical facility where the patient has been taken. Alternatively, this information is transmitted wirelessly to the medical facility.

As will be appreciated by one skilled in the art based on this disclosure, aspects of the present invention may be embodied as a system, method or computer program product. Accordingly, aspects of the present invention may take the form of an entirely hardware embodiment, a processor operating with a software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store, a program for use by or in connection with an instruction execution system, apparatus, or device. The above examples of computer readable storage medium are also examples of the storage of the above discussed embodiments.

Computer program code for carrying out operations for aspects of the present invention may be written in any combination of one or more programming languages, including an object oriented programming language such as Java, Smalltalk, C++, C#, or the like and conventional procedural programming languages, such as the "C" programming language or similar programming languages. The program code in at least one embodiment executes entirely on the compact, portable computer as a stand-alone software package.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations or subcombinations of blocks in the block diagrams and/or flowchart illustration, can be implemented by special purpose hardware-based systems that perform the specified functions or acts, or combinations of special purpose hardware and computer instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture, including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
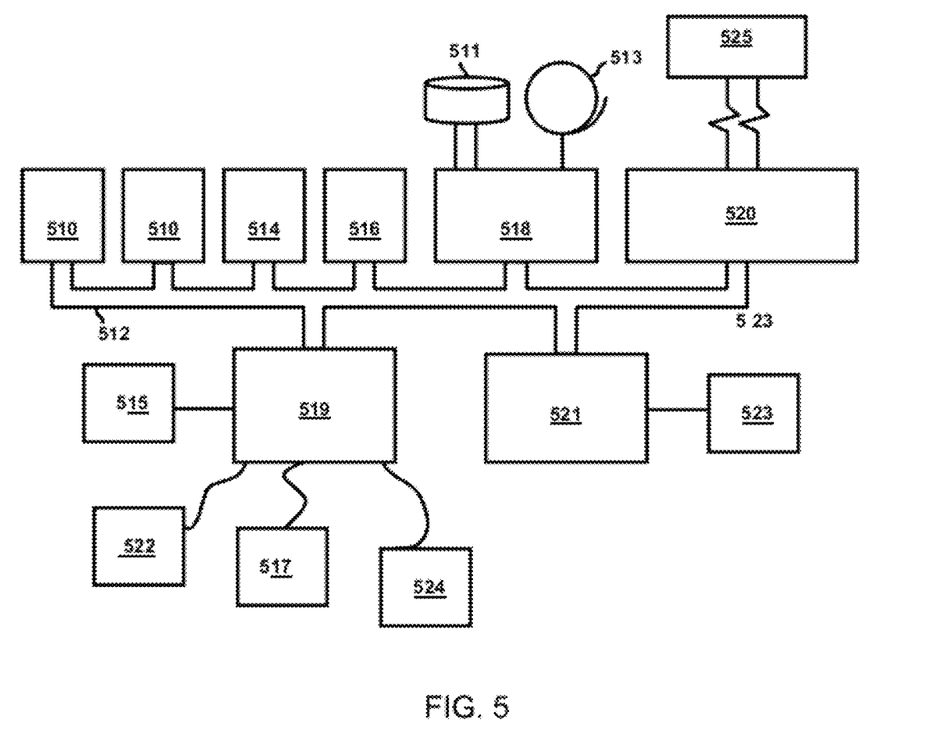
FIG. 5 illustrates a computer program product and computer implementation according to an embodiment of the invention.

FIG. 5 illustrates an example hardware environment for practicing at least one embodiment of the invention. This schematic drawing illustrates a hardware configuration of an information handling/computer system in accordance with at least one embodiment of the invention. The system comprises at least one processor or central processing unit (CPU) 510. The CPUs 510 are interconnected with a system bus 512 to various devices such as a random access memory (RAM) 514, a read-only memory (ROM) 516, and an input/output (I/O) adapter 518. The I/O adapter 518 can connect to peripheral devices, such as disk units 511 and tape drives 513, or other program storage devices that are readable by the system. The system can read the inventive instructions on the program storage devices and follow these instructions to execute the methodology of at least one embodiment of the invention. The system further includes a user interface adapter 519 that connects a keyboard 515, a mouse 517, a speaker 524, a microphone 522, and/or other user interface devices such as a touch screen device (not shown) to the bus 512 to gather user input. Additionally, a communication adapter 520 connects the bus 512 to a data processing network 525, and a display adapter 521 connects the bus 512 to a display device 523, which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

We claim:

1. A system for receiving an output from an external source comprising:
   a storage configured to store at least one algorithm;
   a communications module for receiving vital-sign data from an external source and storing the received vital-sign data in said storage;
   an analysis controller in communication with said storage, said analysis controller monitors said storage;
   a test module in communication with said analysis controller and said storage, said test module configured to receive at least a portion of the vital-sign data from said storage through said analysis controller and to store any output produced by said test module in said storage, and
   said test module includes running means for running said at least one algorithm loaded into said storage where said at least one algorithm processes at least a portion of the vital-sign data provided by said analysis controller; and
   a ruggedized, compact housing enclosing said storage, said communications module, said analysis controller, and said test module.

2. The system according to claim 1, further comprising a connector passing through a wall of said housing and in communication with said communications module.

3. The system according to claim 1, further comprising a display in communication with said test module for displaying at least part of the output produced by said test module.

4. The system according to claim 1, wherein said storage includes at least one database.

5. The system according to claim 1, wherein said storage includes at least one database configured to store the received vital-sign data and at least one database configured to store the output of said test module.

6. A system for receiving vital-sign information from a vital-sign monitor, said system comprising:
   a storage having at least one database, said storage configured to store at least one algorithm;
   a communications module for receiving vital-sign data from an external source and storing the received vital-sign data in said database of said storage;
   an analysis controller in communication with said storage, said analysis controller monitors said storage;
   a test module in communication with said analysis controller and said storage, said test module configured to receive at least a portion of the vital-sign data from said storage through said analysis controller, and
   said test module includes running means for running said at least one algorithm loaded into said storage where said at least one algorithm processes at least a portion of the vital-sign data provided by said analysis controller, said running means provides an output in substantially real time from receipt of the vital-sign data by said communications module;
   a ruggedized, compact housing enclosing said storage, said communications module, said analysis controller, and said test module.

7. The system according to claim 6, further comprising a connector passing through a wall of said housing and in communication with said communications module.

8. The system according to claim 7, further comprising a display in communication with said test module for displaying at least part of the output produced by said test module.

9. The system according to claim 8, wherein said storage includes at least one database configured to store the received vital-sign data and at least one database configured to store the output of said test module.

10. The system according to claim 9, wherein said test module stores in said storage the output produced by the at least one algorithm.

11. The system according to claim 6, further comprising a display in communication with said test module for displaying at least part of the output produced by said test module.

12. The system according to claim 6, wherein said storage includes at least one database configured to store the received vital-sign data and at least one database configured to store the output of said test module.

13. The system according to claim 6, wherein said test module stores in said storage at least part of the output produced by the at least one algorithm.

14. The system according to claim 13, wherein said storage includes at least one database configured to store the received vital-sign data and at least one database configured to store the output of said test module.

* * * * *